United States Patent [19]

Gustavsson

[11] Patent Number: 4,673,404
[45] Date of Patent: Jun. 16, 1987

[54] PRESSURE BALANCING DEVICE FOR SEALED VESSELS

[76] Inventor: Bengt Gustavsson, Bergsbogatan 29, S-421 79 Västra Frölunda, Sweden

[21] Appl. No.: 700,699
[22] PCT Filed: May 21, 1984
[86] PCT No.: PCT/SE84/00195
    § 371 Date: Jan. 17, 1985
    § 102(e) Date: Jan. 17, 1985
[87] PCT Pub. No.: WO84/04672
    PCT Pub. Date: Dec. 6, 1984

[30] Foreign Application Priority Data

May 20, 1983 [SE] Sweden .................. 8301176
Mar. 2, 1984 [SE] Sweden ............ PCT/SE84/00075

[51] Int. Cl.⁴ .................. A61B 19/00; A61M 5/32
[52] U.S. Cl. .................. 604/411; 604/415
[58] Field of Search .................. 604/411, 415, 416

[56] References Cited

U.S. PATENT DOCUMENTS

| 1,413,703 | 4/1922 | Biehn | 604/415 |
| 2,326,490 | 8/1943 | Perelson | 604/411 |
| 2,524,364 | 10/1950 | Smith | 604/415 |
| 2,524,365 | 10/1950 | Smith | 604/415 |
| 2,608,972 | 9/1952 | Chrigstrom | 604/415 |
| 2,771,074 | 11/1956 | Landsperger et al. | 604/411 |
| 2,777,443 | 1/1957 | Thomas et al. | 604/411 |
| 2,833,281 | 5/1958 | Krug | 604/411 |
| 2,851,201 | 9/1958 | Poitras et al. | 604/411 |
| 3,940,003 | 2/1976 | Larson | 604/411 |
| 4,507,113 | 3/1985 | Dunlap | 604/411 |
| 4,564,054 | 1/1986 | Gustavsson | 604/411 |

FOREIGN PATENT DOCUMENTS 0091312 10/1983 European Pat. Off. .
7400110 1/1974 France .
341982 1/1972 Sweden .

Primary Examiner—Stephen C. Pellegrino
Assistant Examiner—Jerome R. Smith, Jr.
Attorney, Agent, or Firm—Cushman, Darby & Cushman

[57] ABSTRACT

Device for ventilating and pressure balancing the interior of a sealed vessel (91) containing a substance which is to be taken out from said vessel e.g. by an injection syringe, said vessel being provided with a closure means (2) comprising a sealing member (2) through which a puncturing member, e.g. a needle can be passed for entering the interior of said vessel the closure means (2) or a connection means (3) attachable onto said vessel is provided with ventilating means (10, 13, 14, 15) arranged to provide a communication between the interior of the vessel (1) and a closed container or alternatively the atmosphere via a filter (16).

8 Claims, 5 Drawing Figures

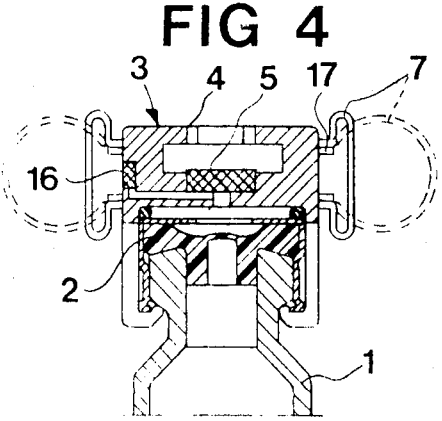
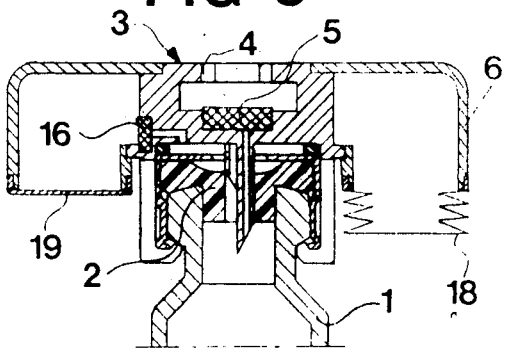
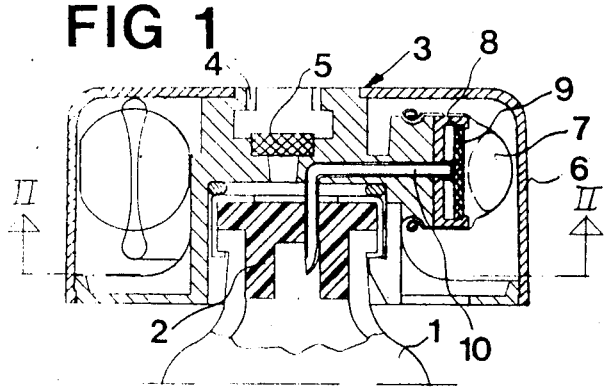
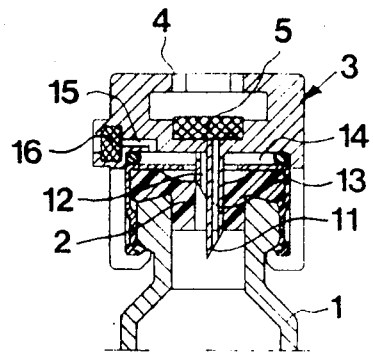
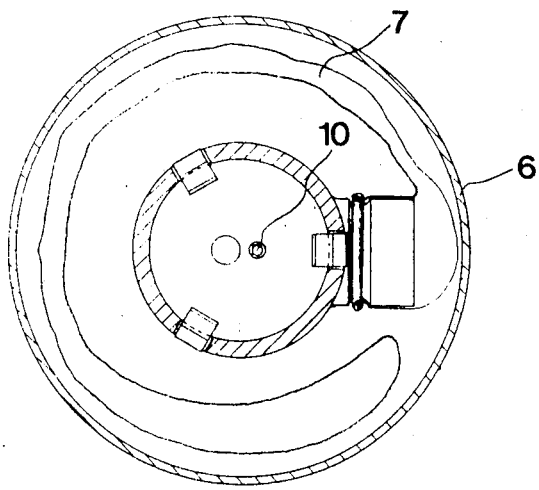

PRESSURE BALANCING DEVICE FOR SEALED VESSELS

TECHNICAL FIELD

The present invention refers to a device for ventilating and pressure balancing the interior of a sealed vessel containing a substance which is to be taken out from said vessel e.g. by an injection syringe, said vessel being provided with a closure means comprising a sealing member through which a puncturing member, e.g. a needle can be passed for entering the interior of said vessel.

BACKGROUND OF THE INVENTION

Drugs and medicines of different kinds which are to be injected into a patient are usually delivered in vials sealed by a membrane or sealing plug which can be penetrated by the needle of an injection syringe. The substances are in some cases delivered as solutions and in other cases as dry substances, which firstly have to be dissolved in a solvent, e.g. water, which is injected into the vial by an injection springe. In both cases there are pressure balancing problems when pressing liquid into or taking liquid out from the air-tightly sealed vial.

THE OBJECT OF THE INVENTION AND ITS MOST IMPORTANT FEATURES

The object of the present invention is to provide a pressure balancing system especially intended for vials containing toxic substances, such as cytoxic drugs, etc., which are not allowed to contaminate the ambient air. This has according to the invention been achieved by the fact that said closure means or a connection means attachable onto said vessel is provided with ventilating means arranged to provide a communication between the interior of the vessel and a closed container or alternatively the atmosphere via a filter.

BRIEF DESCRIPTION OF THE DRAWINGS

FIG. 1 is a longitudinal section of a closure means to a vial according to the present invention, FIG. is a section according to the line II—II in FIG. 3, FIGS. 3–5 is a longitudinal sections through three other embodiments.

DESCRIPTION OF SOME EMBODIMENTS

Referring to the drawings the numeral 1 denotes a vial sealed by a stopper 2. A connection means 3 is attached to the bottle-neck of the vial 1. The connection means 3 has a bayonet coupling 4 for receiving a transferring member (not shown) of the kind disclosed in the Swedish patent application No. 8301176-7 and International patent application No. PCT/SE84/00075 and for transferring the content of the vial to an injection syringe without any contamination risk. A sealing member 5, e.g. of Teflon R, which can be penetrated by a needle is provided in the connection means 3, which further is provided with a hood 6 extending radially a considerably distance outside the bottle-neck of the vial 1. A torus-shaped expandable balloon 7 is placed under the hood 6 and attached to a cylindrical balloon attachment 8 provided with a liquid-rejecting filter 9. The balloon 7 communicates with the interior of the vial 1 via a hollow needle 10 passed through the stopper 2.

The balloon attachment 8 could of course be angled at which angling of the balloon 7 is avoided.

The balloon 7 works as a pressure equalizer when handling the contents of the vial 1. In case the vial 1 contains a dry substance this must firstly be dissolved in a solvent, e.g. water, which is injected with an injection syringe. This will create an overpressure in the vial 1 and the surplus air is then pressed into the balloon 7. On sucking up the dissolved substance into the injection syringe air is sucked back into the vial from the balloon and a negative pressure is avoided. A completely closed pressure equaliztion system has thus been achieved.

In inflated condition the walls of the balloon 7 are stretched and they exert a counter-pressure on the volume of air contained therein.

According to the embodiment shown in FIG. 3 the connection means 3 is provided with a pointed member 11 passed through the stopper 2 of the vial 1. The pointed member 10 is provided with two passages 12 and 13, one 12 for a needle (not shown) for transferring the substance contained in the vial to an injection syringe and the other 13 for ventilating the vial 1. The ventilating passage 13 communicates with a free space 14 between the connection means 3 and vial 1 and a further passage 15 in the connection means 3. Said further passage 15 communicates with the atmosphere via a liquid-rejecting filter 16. This filter is preferably of a type also preventing the vapour of the substance contained in the vial to pass therethrough, which is especially important if the substance is toxic. An example of such a filter is HEPA—high efficiency particulate air filter of 10.3 micron.

In FIG. 4 is shown an embodiment similar to the one according to FIG. 3, but it lacks the pointed member 11. Communication between the interior of the vial 1 and the passage 14 can be achieved by the needle (not shown) for transferring the substance to an injection syringe. Said needle can be provided with ventilation means of different kinds as described in the International Application No. PCT/SE84/00075.

The connection means 3 is further on its outside provided with a ring-shaped attachment 17 for a ring-shaped flexible member 7 inflatable like a balloon and arranged to cover the filter 16.

In FIG. 5 is shown a combination of two further embodiments similar to the one according to FIG. 1, but here according to one of the embodiments the flexible member communicating with the interior of the vial 1 via the hollow needle 10 consists of a bellows 18 instead of a balloon 7. The bellows 18 is attached to the lower edges of the hood 6 so that a closed space is provided under said hood. The bellows is pressure-less both in retracted and extended condition. Instead of a bellows a piston-cylinder or similar arrangement, the volume of which is variable, can be used. According to the other embodiment shown in FIG. 5 the interior of the vessel communicates with a space closed by a lid 19 and the volume of which is constant. If the volume of said space is sufficient it can serve as a pressure-balancer or buffer for the vessel.

The invention is of course not limited to the embodiments shown and described, but a number of modifications are possible within the scope of the claims. Thus in cases where nontoxic substances are handled the membrane 5 and coupling means 4 for a transferring member can be eliminated.

I claim:

1. In combination with a vessel having a neck fitted wth a closure member through which a needle can be passed for entering the interior of the vessel for removing or adding material thereto: a device for ventilating and pressure balancing the interior of the vessel comprising a cap fitted and sealed to the neck of the container and overlying the closure member, said cap including an internal passage adapted to be in communication with the interior of the vessel when the closure is punctured and a closed expandable and contractable container in communication with said internal passage.

2. Apparatus according to claim 1, characterized in, that said container includes a balloon (7) having extensible side walls and which in inflated condition exerts a counterpressure on the volume of air contained therein.

3. Apparatus according to claim 1, characterized in, that said container includes a bellows (18), the volume of which is variable and which is pressure-less in both retracted and extended position.

4. Apparatus according to claim 1, characterized in, that said cap (3) is provided with a hollow needle (11) arranged to penetrate the sealing member (2) of the vessel (1) when attaching the connection means to the vessel, said needle constituting said ventilating means.

5. Apparatus as in claim 1 wherein said internal passage is the bore of a hollow member extending through the closure member and having an open end in communication with the interior of the vessel and having an opposite end in communication with the interior of said container.

6. A device for pressure balancing the interior of a vessel having a neck fitted with a closure member through which a needle can be passed for entering the interior of the vessel for removing material from the vessel or adding material to the vessel thereby changing the pressure within the vessel, said device comprising a cap having a recess adapted to be fitted around the neck of the vessel and over the closure member, said cap including an internal passage having an open end adapted to be in communication with the interior of the vessel when a needle passed through the closure member withdraws or adds material to the vessel thereby changing its internal pressure said cap including a closed expandable and contractable container connected to the opposite end of said passage for equalizing the internal vessel pressure.

7. A device as in claim 6 wherein said closed container is an expandable and contractable container.

8. A device as in claim 6 wherein said internal passage is the bore of a hollow member extending through the closure member of the vessel.

* * * * *